(12) United States Patent
Kim et al.

(10) Patent No.: US 8,673,600 B2
(45) Date of Patent: Mar. 18, 2014

(54) METHOD AND APPARATUS FOR PRODUCING LACTIC ACID

(71) Applicant: Hyundai Motor Company, Seoul (KR)

(72) Inventors: Si Hwan Kim, Gyeonggi-do (KR); Chae Hwan Hong, Gyeonggi-do (KR); Jiyoun Seo, Gyeonggi-do (KR); Do Suck Han, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 0 days.

(21) Appl. No.: 13/717,947

(22) Filed: Dec. 18, 2012

(65) Prior Publication Data

US 2013/0266996 A1    Oct. 10, 2013

(30) Foreign Application Priority Data

Apr. 5, 2012    (KR) .................... 10-2012-0035702

(51) Int. Cl.
*C12P 7/56* (2006.01)
*C12P 7/40* (2006.01)
*C12P 7/00* (2006.01)

(52) U.S. Cl.
USPC ............................ 435/139; 435/132; 435/136

(58) Field of Classification Search
USPC ....................................................... 435/139
See application file for complete search history.

(56) References Cited

U.S. PATENT DOCUMENTS

| 4,767,426 A | * | 8/1988 | Daly et al. ...................... 55/487 |
| 4,771,001 A | * | 9/1988 | Bailey et al. ................. 435/139 |
| 5,110,319 A | * | 5/1992 | Turpin et al. ..................... 44/451 |

FOREIGN PATENT DOCUMENTS

| JP | 2009142265 A | 7/2009 |
| JP | 2009261360 A | 11/2009 |
| JP | 2010000025 A | 1/2010 |
| KR | 94-702549 | 8/1994 |
| WO | 2009/099044 A1 | 8/2009 |

OTHER PUBLICATIONS

Moldes et al "Recovery of lactic acid from simultaneous saccharification and fermentation media using anion exchange" 2003 Bioprocess Biosyst Eng 25, 357-363.*

* cited by examiner

*Primary Examiner* — John S Brusca
*Assistant Examiner* — Gerard Lacourciere
(74) *Attorney, Agent, or Firm* — Edwards Wildman Palmer LLP; Peter F. Corless

(57) ABSTRACT

Disclosed is an apparatus and a method for producing lactic acid, wherein only lactic acid is selectively absorbed and separated from fermentation liquor using a lactic acid absorption resin and wherein a neutralizing agent is not used. The present invention does not include a neutralizing process and a process of converting lactate to lactic acid. The method comprises: adding and mixing a culture medium, microorganism and sugar in a fermenter; passing a fermentation liquor through a microorganism filtration unit to remove microorganisms; and selectively absorbing and separating lactic acid from filtered liquid using a lactic acid absorption resin. The apparatus includes a fermenter for lactic acid fermentation; a filtration unit for removing a microorganisms from the fermentation liquor; and a lactic acid absorption resin for selectively absorbing lactic acid from the filtered liquid.

9 Claims, 4 Drawing Sheets

METHOD AND APPARATUS FOR PRODUCING LACTIC ACID

CROSS-REFERENCE TO RELATED APPLICATION

This application claims under 35 U.S.C. §119(a) the benefit of Korean Patent Application No. 10-2012-0035702 filed on Apr. 5, 2012, the entire contents of which are incorporated herein by reference.

BACKGROUND (a) Technical Field

The present invention provides an apparatus and a method for producing lactic acid. In one aspect, it relates to an apparatus and a method for economically producing D-type lactic acid that can be used as raw material for making D-type poly-lactic acid, which can be used as a starting material for producing a stereo-complex poly-lactic blend, a highly potential plant-based material useful as a decoration material for interior/exterior of a vehicle.

(b) Background of the Invention

Among biomass polymers, poly-lactic acid (PLA) is a linear aliphatic polyester and a thermoplastic polymer material, which can be synthesized using monomers obtained from 100% reproducible resources, such as, potato starch and corn starch.

Lactic acid has two stereoisomers, L-type and D-type, with different optical activities. D-type lactic acid can be used for manufacturing D-type poly-lactic acid, which can be used for producing the stereo-complex poly-lactic acid blend, a plant-based material useful to decorate the interior/exterior of a vehicle.

Korean Patent Application Publication No. 2010-0110345 discloses a method for producing lactic acid at a low cost through a continuous fermentation. The lactic acid as produced has a long-term storage stability.

The above mentioned reference discloses, as demonstrated in FIG. 1, a method for producing lactic acid including the steps of: producing a fermentation liquor by adding a culture medium and a neutralizing agent into a fermenter for fermentation; removing microorganisms from the fermentation liquor using a porous membrane filter with an average pore-diameter ranging from 0.01 μm to 1 μm; and extracting lactate from the filtered liquid (i.e., the fermentation liquor) where the microorganisms are removed, and recycling non-filtered liquid by adding into the fermenter for fermentation. In this process, a yeast is used as a microorganism for fermentation, and a culture medium equivalent in volume to that of the extracted fermentation liquor is added into the feremenfer.

However, the use of a yeast for the lactic acid fermentation requires a neutralization step because the yeast is vulnerable to acidic conditions that would be caused by produced lactic-acid. Moreover, the synthesis of poly-lactic acid requires an additional process, which involves replacing lactic acid with neutralized lactate, thereby increasing the manufacturing cost. Further, as protein and sugar sources will remain in the filtered liquid in the fermenter, the excess sources also attribute an increased cost for raw materials.

The above information disclosed in this Background section is intended only for a better understanding of the present invention. At no time, it may be construed as the Applicants' admission of the prior art that is apprised by a person of ordinary skill in the art.

SUMMARY OF THE INVENTION

The present invention has been made in an effort to solve the above-described problems.

In one aspect, the present invention provides an apparatus and a method for producing lactic acid, during which lactic acid is selectively absorbed and separated from a fermentation liquor using a lactic absorption unit (such as, a resin). In general, the method of the invention does not use a neutralization agent, therefore obviating a need for an additional neutralization step which replaces lactic acid with lactate. Thus, the process of separating and purifying lactic acid from the fermentation liquor for use in a later polymerization is made simpler, thereby reducing the manufacturing cost.

In another aspect, the present invention provides an apparatus and a method for producing lactic acid, during which a fermentation liquor is recycled without incurring any loss of nutrient components except for lactic acid, thereby minimizing that volume loss of the raw material. It is thus believed that the increase in the cost for raw materials may be prevented.

In one aspect, the present invention provides an apparatus for producing lactic acid, comprising: a fermenter for use in a lactic acid fermentation using a microorganism; a filtration unit for removing the microorganism present in a fermentation liquor that is produced in said fermenter; and a lactic acid absorption resin for selectively absorbing lactic acid from a filtered liquid, from which the microorganism is removed by the microorganism filtration unit.

In an embodiment, the microorganism filtration unit is made in the form of a tube or a cartridge, which can be inserted into a housing so that the microorganism filtration unit can be replaced.

In another embodiment, the microorganism filtration unit and the lactic acid absorption resin are concentrically arranged in a housing. The fermentation liquor flows from the microorganism filtration unit to the lactic acid absorption resin in a radial direction of the housing. Accordingly, the microorganism can be removed from the fermentation liquor through a cross-flow filtration (CFF).

In still another embodiment, the lactic acid absorption resin is selected from active carbon, neutral resin and anion-exchange resin.

In yet another embodiment, the apparatus further comprises: a lactic acid supply line connecting the fermenter to the microorganism filtration unit to supply the fermentation liquor to the microorganism filtration unit; and a filtered liquid recirculation line connecting the microorganism filtration unit and the lactic acid absorption resin to the fermenter to recirculate the filtered liquid and non-filtered liquid back to the fermenter.

In still yet another embodiment, the microorganism filtration unit and the lactic acid absorption resin may be combined and designed as a single microorganism filtration unit that including the lactic acid absorption resin. Alternately, the microorganism filtration unit and the lactic acid absorption resin can be separately provided as a microorganism filter device and a lactic acid absorption device. These devices may be used for facilitating the recovery of lactic acid and the replacement of the lactic acid absorption resin.

In another aspect, the invention provides a method for producing lactic acid comprising steps of: adding and mixing a culture medium, a microorganism, and sugar in a fermenter for fermentation of lactic acid to produce a fermentation liquor; passing the obtained fermentation liquor through a microorganism filtration unit to remove microorganism through a cross-flow filtration; and, selectively absorbing and separating lactic acid from the filtered liquid, from which the microorganism is removed by a lactic acid absorption resin.

In still another aspect, the method further includes a step of recycling the non-filtered liquid and filtered liquid back to the fermenter through a filtered liquid re-circulation line, wherein the non-filtered liquid has not been subject to the microorganism removal after selectively absorbing lactic acid, and wherein the filtered-liquid has been subject to the lactic acid absorption and removal after the microorganism is removed.

In yet another aspect, additional lactic acid may be produced by adding sugar to the fermenter after lactic acid is absorbed.

In yet still another aspect, lactic acid may be used depending on the rate of lactic acid produced by the lactic acid fermentation.

Other aspects and embodiments of the invention are discussed infra.

The method and the apparatus for producing lactic acid according to the present invention offer advantages provided herein below:

After removing the microorganism from the fermentation liquor that has undergone the lactic acid fermentation, only lactic acid is selectively absorbed and recovered by using a lactic acid absorption resin. Also, the filtered liquid with lactic acid removed is recycled into a fermenter without incurring any loss in volume. Accordingly, lactic acid can be produced by initially adding a culture medium to the maximum level without any further additions. Thus, it is possible to improve the production efficiency of the lactic acid fermentation. Also, it is possible to significantly reduce the time and the cost associated with a process of separating lactic acid from the fermentation liquor.

For instance, compared to those provided by prior art methods, the concentration of lactic acid per fermentation volume may be improved by about 20%. Further, compared to the prior art methods which require a sterilization of additional medium thereby incurring additional process cost, more than 15% of medium used for the fermentation may be saved in accordance with the present invention, since the same medium and the same microorganism can be used.

Further, since lactic acid produced in the fermentation process is directly extracted from the fermentation liquor without the use of a neutralizing agent, a process for obtaining pure lactic acid from lactate produced by the neutralization (such as, electrodialysis or electrodialytic water splitting) is not required. Accordingly, the separation and purification process for a polymerization can be fairly simple, thereby reducing the manufacturing cost.

Additionally, the ion concentration of $Na^+$ and $NH_3^+$ cations of the basic substance used for neutralization of the produced lactic acid, will not be too high to cause a rapid decrease in the degradation activity of the microorganism for the fermentation of lactic acid.

The above and other features of the invention are discussed infra.

BRIEF DESCRIPTION OF THE DRAWINGS

The above and other features of the present invention are described in detail with reference to certain embodiments and accompanying drawings thereof. The embodiments and drawings are given by way of illustration only. They are not intended to be limitative of the present invention.

Figure 1:
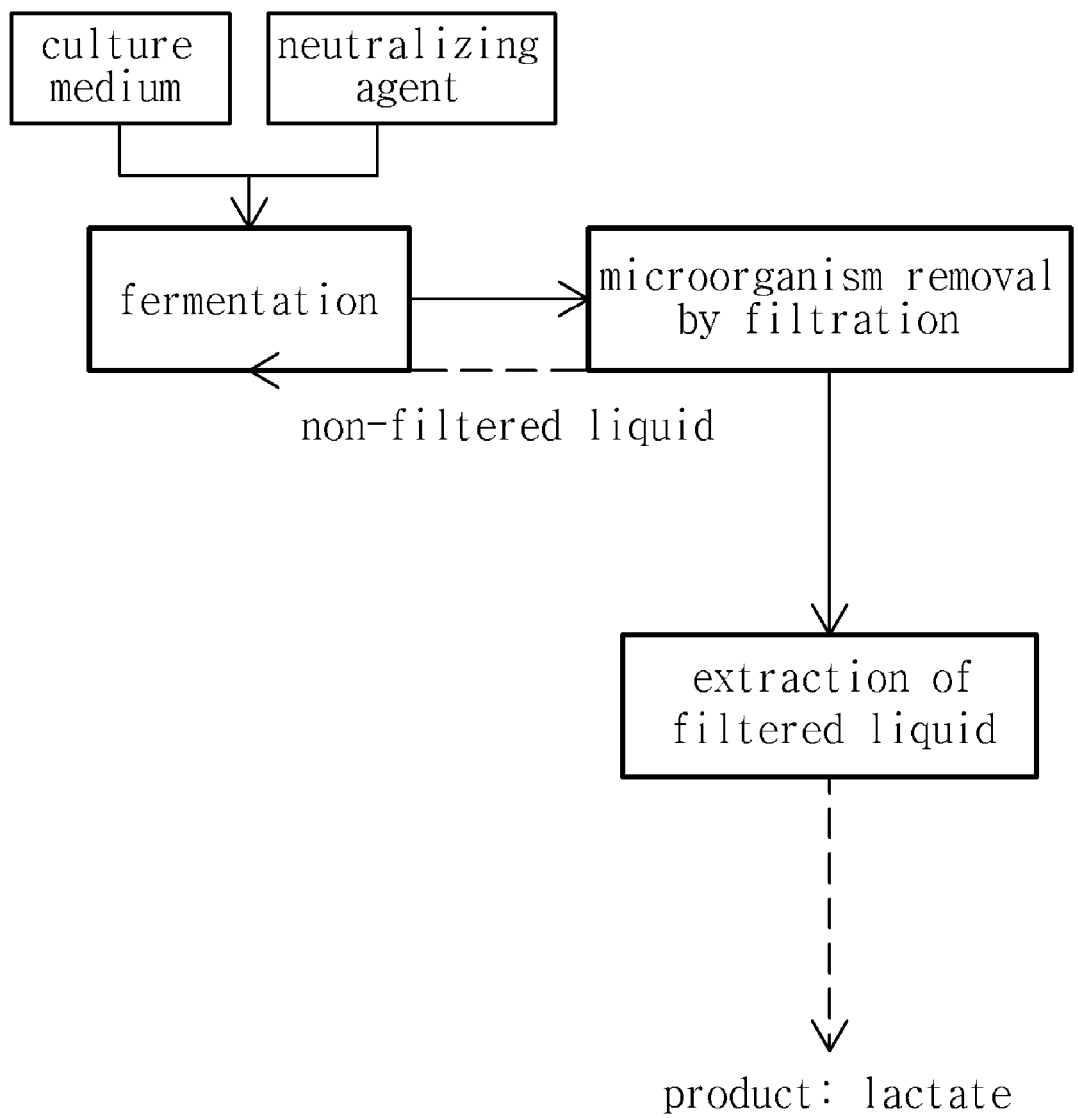
FIG. 1 is a flow chart illustrating a known method for producing lactic acid.

Reference numerals set forth in the Drawings includes reference to the following elements as further discussed below:

It should be understood that the appended drawings are not necessarily to scale, presenting a simplified representation of various features illustrative of the basic principles of the invention. The specific features of the present invention as disclosed herein, including, for example, specific dimensions, orientations, locations, and shapes will be determined in part by a particularly intended application and a use environment.

In the figures, reference numbers refer to the same or equivalent parts of the present invention throughout the several figures of the drawing.

DETAILED DESCRIPTION

Hereinafter reference is made in detail to various embodiments of the present invention, and examples that are illustrated in the drawings and described below. While the invention will be described in conjunction with exemplary embodiments, it should be understood that present description is not intended to limit the invention to those embodiments. On the contrary, the invention is intended to cover not only the exemplary embodiments, but also various alternatives, modifications, equivalents and other embodiments. Such equivalents are considered to be within the scope of this invention and are covered by the claims provided below.

Figure 2:
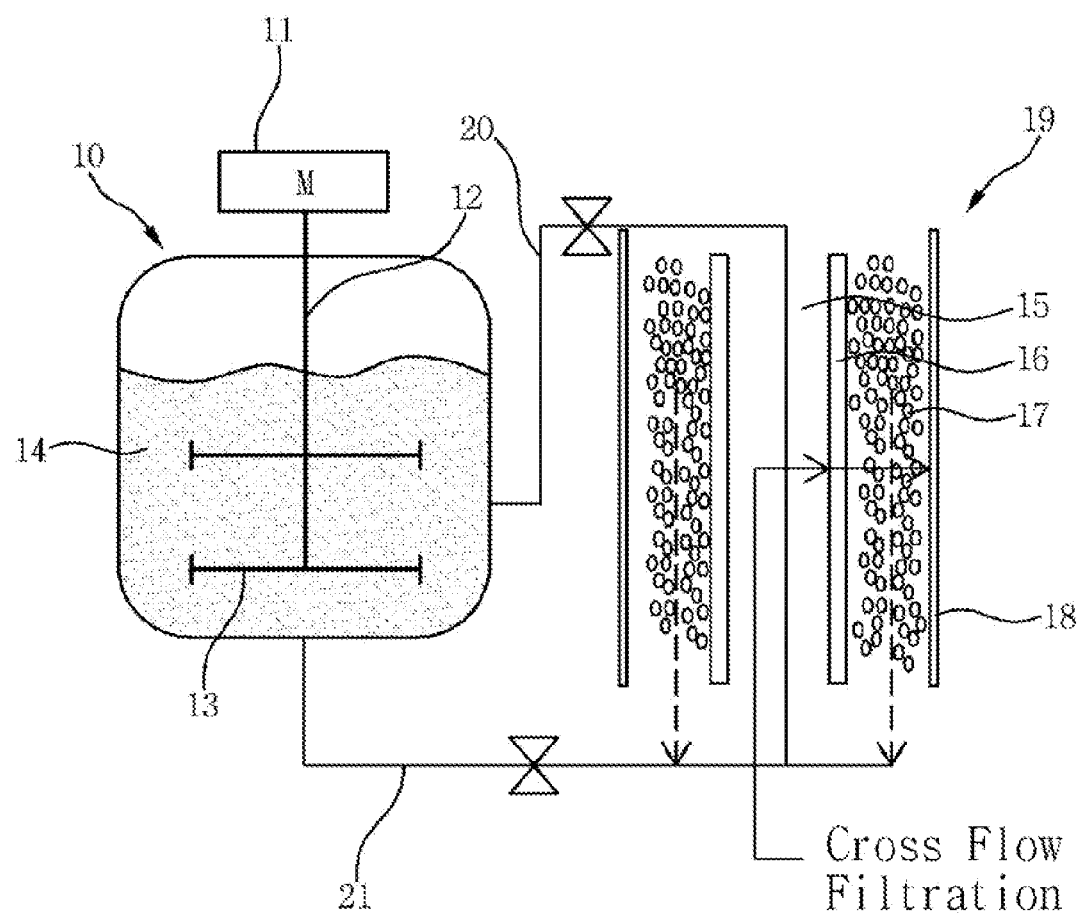
FIG. 2 is a system configuration of an apparatus for producing lactic acid according to an embodiment of the present invention.

FIG. 2 is a system configuration of an apparatus that can be used for producing lactic acid according to an embodiment of the present invention.

In one embodiment, the present invention provides an apparatus and a method for producing lactic acid wherein lactic acid produced in the process of the fermentation is recovered by absorption.

The apparatus for producing lactic acid according to the present invention includes: a lactic acid fermentation unit for performing the fermentation of lactic acid; and a microorganism removal and lactic acid absorption-unit (19) for selectively absorbing lactic acid after strain is separated.

The lactic acid fermentation unit includes: a fermenter (10) provided with a storage space for storing culture medium; an agitator (13) rotatably installed in the fermenter (10) for uniformly agitating contents; and a motor (11) for driving the agitator (13).

An upper cover is detachably installed on the top of the fermenter (10) to open and close the fermenter, so that contents can be added into the fermenter.

Further, the fermenter (10) includes an outlet for discharging a fermentation liquor (14) at a lower end of one side, and an inlet for circulating a filtered liquid into the fermenter (10) at its lower end.

The agitator (13) includes a center axis (12) extending in a vertical direction in the fermenter (10), and a blade extending from the center axis (12) in a radial direction so that the contents may be agitated.

The motor (11) is connected to an upper end of the center axis (12) of the agitator (13). The agitator receives driving force from the motor (11), thereby rotating the blade and agitating the contents in the fermenter (10).

The fermentation liquor (14) produced in the fermenter (10) can be sent to the microorganism removal and lactic acid-absorption unit (19) through the connection between the lactic acid fermentation unit and the microorganism removal and lactic acid-absorption unit (19), while the remaining filtered liquid with lactic acid being removed and the non-filtered liquid can be recycled back to the lactic acid fermentation unit.

To perform this operation, the outlet of the fermenter (10) is connected to an inlet for the fermentation liquor (14) of the lactic acid absorption unit (19) through a lactic acid supply line. Through the connection, the fermentation liquor (14) produced in the fermenter (10) can be sent to the microorganism removal and lactic acid-absorption unit (19). The inlet of the fermenter (10) is connected to an outlet for the filtered liquid of the microorganism removal and lactic acid absorption unit (19) through a filtered liquid recirculation line, so that the remaining filtered liquid with lactic acid removed and the non-filtered liquid can be recycled to the lactic acid fermentation unit.

Valves are provided in the lactic acid supply line and the filtered liquid recirculation line. The amount of the fermentation liquid (14) flowing through the lactic acid supply line and the filtered liquid flowing through the filtered liquid recirculation line thereby can be controlled.

The microorganism removal and lactic acid absorption unit includes: a housing (18) configuring an outer shaper and protecting the contents against an external impact; a microorganism filtration unit (such as, a membrane) (16) installed in the housing (18); and a lactic acid-absorption resin (17) inserted between the housing (18) and the microorganism filtration unit (16).

The housing includes an inlet for the fermentation liquor (14) formed at its upper part to supply the fermentation liquor (14) and an outlet for the filtered liquid formed at its lower part to discharge the non-filtered liquid and the filtered liquid.

The microorganism filtration unit (16) may remove microorganism from the fermentation liquor (14) through the cross-flow filtration. For example, in a case that a membrane is used, the fermentation liquor (14) flows in a direction of the membrane thickness (or in a direction crossing the membrane).

The cross-flow filtration offers certain advantages with regard to the sterilization and the efficiency.

To be compatible with the system, the microorganism filtration unit (16) may be either in the form of a tube, in which, for example, a membrane having a circular shape is used, or a cartridge, in which, for example, a membrane that is automatically wound and unwound is used.

According to an embodiment of the present invention, the microorganism filtration unit (16) separates the interior of the housing (18) into a passage for the non-filtered liquid and a passage (15) for the filtered liquid.

The passage for the non-filtered liquid is formed in the microorganism filtration unit (16) to allow the fermentation liquor (14) introduced through the inlet of the fermentation liquor (14) to flow along the microorganism filtration unit (16). The passage (15) for the filtered liquid is formed between the housing (18) and the microorganism filtration unit (16) to allow passage of the filtered liquid, from which microorganism is removed by the microorganism filtration unit (16).

The lactic acid absorption resin (17) is inserted between the microorganism filtration unit (16) and the housing (18). Active carbon, neutral resin (Amberlite XAD 1600) and anion-exchange resin, can be used to selectively absorb lactic acid that is recovered from the filtered liquid, from which the microorganism is removed by the microorganism filtration unit (16).

The lactic acid absorption resin (17) provided herein is in the form of small-sized spherical granules. However, it is understood that there is no limitation with respect to the size and the shape of the lactic acid absorption resin that can be used.

Although the microorganism filtration unit (16) and the lactic acid absorption resin (17) are provided in the form of a single cartridge, they can be provided in separate units including, such as, a filtration unit) and a lactic acid absorption unit. Accordingly, the microorganism filtration unit and the lactic acid absorption resin can easily be cleaned to remove foreign materials, (e.g., microorganisms) accumulated in the filtration unit. Or the entire filtration unit can be easily replaced, if necessary, to ensure an easy maintenance.

On the other hand, in case the microorganism filtration unit (16) and the lactic acid absorption resin (17) are together provided in a single device, the filtration unit must be separated from the lactic acid absorption unit, thus making the feature more complex. The operation requires inserting the filtration unit into and detaching it from the housing Therefore, by providing separately an independent filtration unit and a lactic acid absorption unit, the above-mentioned problem can be avoided.

Figure 3:
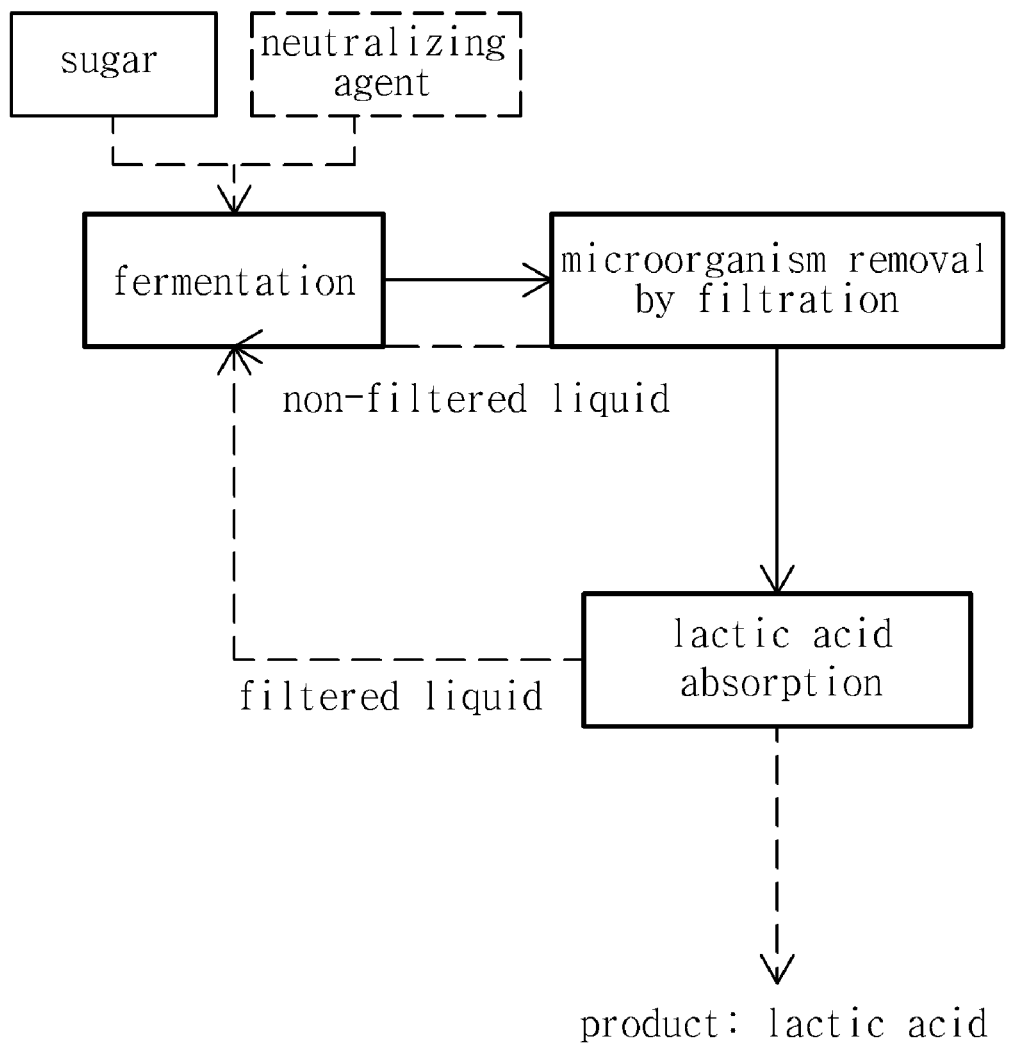
FIG. 3 is a flow chart of a method for producing lactic acid according to an embodiment of the present invention; and, FIG. 4 is a graph illustrating the relationship between a population of microorganism and the concentration of lactate.
Figure 4:
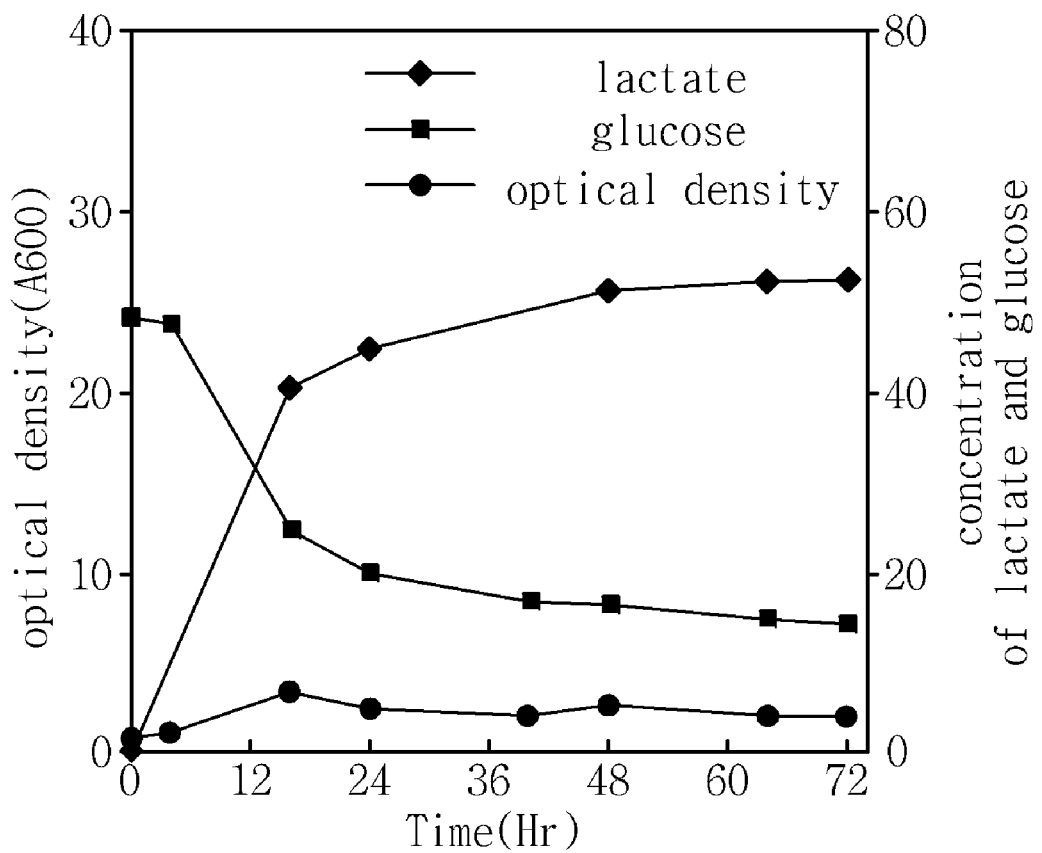

FIG. 3 shows a flow chart illustrating a method for producing lactic acid according to an embodiment of the present invention, and FIG. 4 shows a graph illustrating the relationship between the microorganism population and the lactate concentration.

The method for producing lactic acid according to the present invention is provided in detail with reference to the apparatus described above.

A culture medium, microorganism and sugar are added to the fermenter (10). These added contents are uniformly agitated by the agitator (13) to carry out the lactic acid fermentation.

Generally, if the lactic acid fermentation is performed through the metabolic process of a microorganism, such as, *Lactobacillus, E. coli*, yeast, etc., the produced lactic acid lowers the pH level in the fermenter (10), which in turn causes damages to the microorganisms and deteriorates the growth of the microorganism. To solve this problem, an appropriate pH level needs to be maintained with the use of a neutralizing agent, such as, sodium hydroxide (NaOH), ammonia, etc. In the present invention, however, lactic acid is directly and selectively extracted from the fermentation liquor (14) without the use of the neutralizing agent.

Unlike the prior art methods, the present invention does not involve an deterioration on the growth of the microorganism and does not require the use of the neutralizing agent. In the prior art methods, since the methods continuously use the fermentation liquor containing lactic acid, the accumulation of lactic acid deteriorates the growth of the microorganism if a neutralizing agent is not used. However, the present invention provides a method during which lactic acid is selectively extracted; thus, the concentration of lactic acid does not increase to be over a certain limit Accordingly, the present invention solves problems, such as, the growth of the microorganism is deteriorated if the neutralizing agent is not used.

The fermentation liquor (14) produced in the fermenter (10) is supplied to the lactic acid inlet of the microorganism removal and lactic acid-absorption unit (19) through the lactic acid supply line, and the fermentation liquor (14) introduced through the lactic acid inlet is absorbed by the microorganism filtration unit (16) through the cross-flow filtration when the non-filtered liquid flows through the passage in the microorganism filtration unit (16) The microorganism is thereby removed from the fermentation liquor (14).

Further, while the filtered liquid that has passed through the microorganism filtration unit (16) flows in a direction crossing the passage (15) for the filtered liquid between the microorganism filtration unit (16) and the housing (18), only lactic acid in the filtered liquid is absorbed by the lactic acid absorption resin (17). The filtered liquid with lactic acid removed and the non-filtered liquid that has not been filtered by the microorganism filtration unit (16) are re-sent to the fermenter (10) through the filtered liquid recirculation line. Accordingly, the fermentation process can be performed without the loss of nutrient components, and with a minimized loss in the volume, of the fermentation liquid (14) (the filtered liquid).

In the prior art, to remove the microorganism from the fermentation liquor (14) of lactic acid through the filter and extracting the filtered liquid a fresh culture medium needs to be added into the fermenter (10) for performing the fermentation. Further, the concentration of the microorganism can be maintained only if the volume of the culture medium is added with a volume equal to that of the filtered liquid extracted after the removal of the microorganism (microorganism removal filtering). Moreover, a large amount of the neutralizing agent is used for neutralizing lactic acid produced by the lactic acid fermentation.

Further, a process for converting lactate to lactic acid, is needed. All the above discussed features attribute an increase in the production cost.

In the present invention, however, only lactic acid is absorbed after the microorganism removal filtering and then the filtered liquid (except lactic acid) is recycled to the fermenter (10). Thus, an equal volume of the fermentation liquid can be maintained. Also, additional lactic acid is produced by converting sugar, such as, glucose, to into lactic acid. Further, the neutralizing agent is rarely used because lactic acid that may increases acidity has been absorbed. In certain embodiments, a neutralizing agent may be used depending on the production rate of lactic acid.

Accordingly, in the present invention, only lactic acid is selectively absorbed and recovered with the use of the lactic acid absorption resin (17) after the microorganism from the lactic acid fermented liquor (14) is removed. The filtered liquid with lactic acid removed is recycled to the fermenter (10) without incurring any loss in the volume. Accordingly, the production efficiency in the lactic acid fermentation can be improved by starting with a maximum amount of a culture medium, thereby obviating any need for further additions of the culture medium. It is also possible to significantly save the time and the cost associated with the process of separating lactic acid from the fermentation liquor.

Compared to the prior art methods, the concentration of lactic acid produced per the fermentation volume may be increased by about 20%. When the prior art methods require additional process cost for sterilizing additional medium, the present invention makes it possible to save more than 15% of the fermentation medium since the same medium and the same microorganism can be used.

Further, because the neutralizing agent is rarely used and lactic acid produced in the fermentation process is directly extracted from the fermentation liquor, the present invention does not include a process (e.g., an electro-dialysis, a water decomposition electro-dialysis, etc.) for obtaining pure lactic acid from lactate that is produced by the neutralization. Thus, the separation and purification process for polymerization is simplified, thereby reducing the process cost.

Additionally, the ion concentration of Na+ and NH3+, each of which is a cation contained in basic substance used in the neutralization of the produced lactic acid, will not be too high to cause a rapid decrease in the degradation activity of the microorganism for the fermentation of lactic acid.

As illustrated in FIG. 4, the optical density cannot increase in a large scale if the lactate concentration increases. In the present invention, however, this problem does not occur because the neutralizing agent is rarely used and lactic acid is directly extracted.

The invention has been described in detail with reference to certain embodiments thereof. However, it will be appreciated by those skilled in the art that changes may be made in these embodiments without departing from the principles and spirit of the invention and are still within the scope of the claims and their equivalents.

What is claimed is:

1. An apparatus for producing lactic acid, comprising a fermenter for lactic acid fermentation using a microorganism;
   a housing;
   a microorganism filtration unit installed in the housing for removing microorganisms present in a fermentation liquor supplied from the fermenter;
   a lactic acid absorption unit inserted between the housing and the microorganism filtration unit;
   wherein the microorganism filtration unit separates the interior of the housing into a passage for non-filtered liquid and a passage for filtered liquid;
   wherein the lactic acid absorption unit is a lactic acid absorption resin for selectively absorbing lactic acid from the filtered liquid, from which the microorganism is removed by the microorganism filtration unit; and
   wherein the apparatus further comprises a lactic acid supply line for supply the fermentation liquor to the passage for the non-filtered liquid, and a filtered liquid recirculation line for recirculating the filtered liquid with lactic acid removed and the non-filtered liquid to the fermenter.

2. The apparatus of claim 1, wherein said microorganism filtration unit is in the form of a membrane and can be inserted into a housing.

3. The apparatus as claimed in claim 1, wherein said microorganism filtration unit is in the form of a tube or a cartridge, and said microorganism filtration unit can be inserted into a housing.

4. The apparatus as claimed in claim 1, wherein said lactic acid absorption resin is selected from active carbon, neutral resin and anion-exchange resin.

5. The apparatus as claimed in claim 1, further comprising a lactic acid supply line connecting said fermenter to said microorganism filtration unit to supply the fermentation liquor to the microorganism filtration unit; and a filtered liquid recirculation line connecting said microorganism filtration unit and said lactic acid absorption resin to said fermenter to recirculate the filtered liquid and the non-filtered liquid to said fermenter.

6. The apparatus as claimed in claim 1, wherein said microorganism filtration unit and said lactic acid absorption resin are concentrically arranged in the housing, and wherein the fermentation liquor flows from the microorganism filtration unit to the lactic acid absorption resin in a radial direction of a housing, thereby the microorganism can be removed from the fermentation liquor through a cross-flow filtration.

7. A method for producing lactic acid using the apparatus in claim 1 comprising steps of:
   adding and mixing a culture medium, a microorganism and sugar in a fermenter to obtain a fermentation liquor for a fermentation of lactic acid;
   passing the fermentation liquor through a microorganism filtration unit to remove the microorganism from the fermentation liquor through a cross-flow filtration to provide filtered liquid;

selectively absorbing and separating lactic acid from the liquid, from which the microorganism has been removed using a lactic acid absorption resin; and recycling non-filtered liquid and the filtered liquid to the fermenter through a filtered liquid recirculation line, wherein the non-filtered liquid has not been subject to the microorganism removal.

8. A method as claimed in claim 7, wherein additional lactic acid is produced by adding sugar to said fermenter after said lactic acid is absorbed.

9. A method as claimed in claim 7, wherein the amount of said lactic acid used is dependent upon a production rate of lactic acid in the lactic acid fermentation.

\* \* \* \* \*